United States Patent [19]

Kleinschmidt et al.

[11] 4,292,499
[45] Sep. 29, 1981

[54] ELECTRONIC CALCIFICATION INDICATOR FOR FLOW HEATERS HEATED BY PTC RESISTORS

[75] Inventors: Peter Kleinschmidt, Munich; Hans Meixner, Haar; Valentin Magori, Munich, all of Fed. Rep. of Germany

[73] Assignee: Siemens Aktiengesellschaft, Berlin and Munich, Fed. Rep. of Germany

[21] Appl. No.: 59,691

[22] Filed: Jul. 23, 1979

[30] Foreign Application Priority Data

Sep. 7, 1978 [DE] Fed. Rep. of Germany ....... 2839062

[51] Int. Cl.$^3$ ................... H05B 1/02; A47J 31/56; A47J 31/88; F24H 1/10
[52] U.S. Cl. ..................................... 219/308; 99/285; 99/288; 219/283; 219/301; 219/505; 219/506; 222/146 HE; 340/606; 340/640
[58] Field of Search ............... 219/308, 309, 301, 302, 219/283, 330, 328, 506; 99/279, 281, 285, 288; 340/640, 606; 222/146 HE, 504, 505

[56] References Cited

U.S. PATENT DOCUMENTS 3,781,839 12/1973 Bodge ................................ 219/308

FOREIGN PATENT DOCUMENTS 2704146 8/1978 Fed. Rep. of Germany ...... 219/308

Primary Examiner—A. Bartis
Attorney, Agent, or Firm—Hill, Van Santen, Steadman, Chiara & Simpson

[57] ABSTRACT

A system is disclosed for indicating when a flow heater used for vaporization of water and heated by PTC resistors as heating elements therein must be decalcified. Within the flow heater a PTC resistor element is located at a water entry and also at a water exit region. A main PTC heater element is also provided between the entry and exit elements. Separate power supply lines are run to the exit and entry heating elements and an electronic circuit is provided which determines when a difference in current flow in the exit heating element compared to the entry heating element exceeds a given value indicative of the need for decalcification. The circuit connects with an indicator which is triggered when decalcification is required.

6 Claims, 3 Drawing Figures

ELECTRONIC CALCIFICATION INDICATOR FOR FLOW HEATERS HEATED BY PTC RESISTORS

BACKGROUND OF THE INVENTION

The invention relates to an electronic calcification indicator.

A significant problem in flow heaters, particularly in those with vaporization of water, is their calcification which hinders functioning thereof. Although there is basically the possibility of decalcifying the water to be supplied to a flow heater in a known manner, such devices are not installed at all points. In particular, this is true for the widespread employment of coffee makers.

For flow heaters with an electrical power output of a magnitude of 500 Watts, the employment of PTC resistor heating elements (also known as ceramic PTC resistance elements on the basis of barium titanate) are being provided to an increasing degree. These PTC resistor heating elements have a self-regulating effect known per se, namely, for example, to heat a liquid into the range of a temperature prescribed by means of the Curie temperature of the PTC resistor material and to then allow no further significant temperature increase to occur by means of a material-dependent step down of the emitted heated capacity.

SUMMARY OF THE INVENTION

An object of the present invention is to specify an electronic indicator to detect occurring calcification of a PTC-resistor-heated flow heater.

This object is inventively achieved with an electronic calcification indicator wherein at least at a region of a water entry and water exit of the flow heater, PTC heating element resistors are provided which each have a separate current supply line. Circuitry is provided for supplying separate currents to each of the current supply lines at the entry and exit regions and circuitry is provided for determining a relative current change in these current supplies so as to establish a signal voltage for activating a display device.

For conventional heating elements with heating wire windings, display devices for excessive calcification are known which are based on the drastic temperature increase in the heating element occurring with such a calcification. With the assistance of simple temperature sensors in the heating element, the overheating can thus be easily determined in such conventional heating elements and be evaluated to form a corresponding signal which indicates that the device is now desparately in need of de-calcification.

In a PTC resistor heating element, however, this technical feature completely fails since, because of the self-regulating property of the PTC resistor material, no significant temperature increase which could be practically employed for a sure display occurs—not even in the actual heating element—no matter how great the calcification.

The present invention is based on a principle which, by comparison is completely different. Here, the technical fact is exploited that, in any flow heater, such as a coffee-maker, the region where the water exits calcifies to a varying degree in comparison to the region where the water enters. Because of the greater calcification at the water exit, although the heat conduction from the PTC resistor element is lower in this area, the heating temperatures are essentially of the same magnitude for the heating elements in both areas.

As a rule, a PTC resistor heater for a flow heater, for example a coffee-maker, is subdivided into a plurality of individual heating elements for the several hundred Watt heat output necessary. These individual heating elements are connected to the power supply parallel to one another. In case of a single PTC resistor element as the heating element, a subdivision of the electrode surfaces of the individual electrodes is provided for the present invention. In constructing the invention, one individual PTC resistor heating element is provided by a physical separation of a resistance layer of a larger PTC resistor at least in the area of the water entry and also in the area of the water exit of the heater. A bottom electrode remains intact while the top electrode is also separated so that separate electrodes are provided on each of the separated resistance layers. For electronic evaluation, the current strengths of the electric currents flowing in these parts of the total heating element are compared with one another. A difference of the current consumption exceeding a predetermined tolerance value or threshold value, or a change of the difference of the current consumption occurring over a period of use may be employed as the evaluation criterion.

DESCRIPTION OF THE PREFERRED EMBODIMENTS

Figure 1:
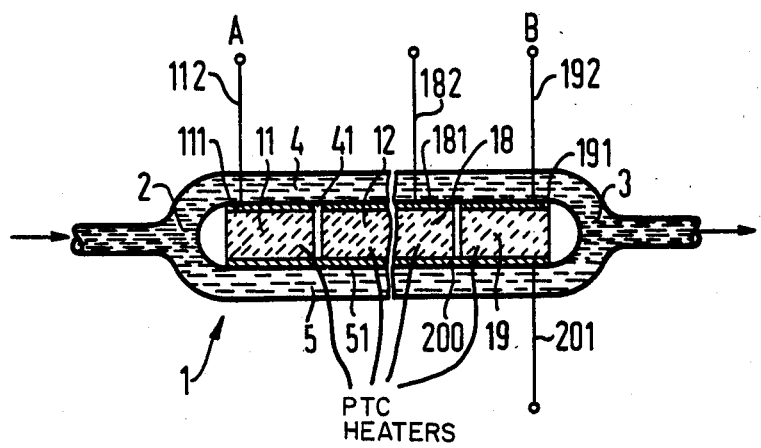
FIG. 1 is a cross-sectional view of the invention.

FIG. 1 shows a flow heater 1 with water entry 2 and water exit 3 in longitudinal fragmental section. The water in the actual heater is subdivided into the branches 4 and 5 and flows over heat contact surfaces 41 and 51 at which individual, preferably plate-shaped PTC resistor heating elements are provided at the inside. Heat-conductive and electrically insulated layers which compensate thermal expansion are also provided at the heating elements. Four heating elements 11, 12, 18 and 19 are illustrated in FIG. 1. The number of the elements omitted in the representation in the central region depends, among other things, on the required total output. Individual PTC resistor heating elements, such as elements 11 through 19, are preferred because, among other things, large-surfaced heating elements are not only more expensive to manufacture, but also are subjected to danger of breakage to a greater degree as a result of thermal tensions. In principle, however, the heating elements 11 through 19 can also be a single piece which has individual electrode areas which correspond, on the one hand to the heating elements 11 and 19 and, on the other hand, to the remaining heating elements grouped together. As shown in principle in FIG. 1, the heating element 11 can be supplied with electric current in the area of the water entry via the electrode referenced 111 and its connection line 112. The corresponding situation is true for the electrode 191 and connection line 192 of the heating element 19. An electrode which, under certain conditions, is continuous or, respectively, electrodes of the heating elements 12 through 18 connected with one another, are referenced 181, 182. The back electrodes can be provided as a common electrode 200 with a corresponding connection line 201.

Figure 2:
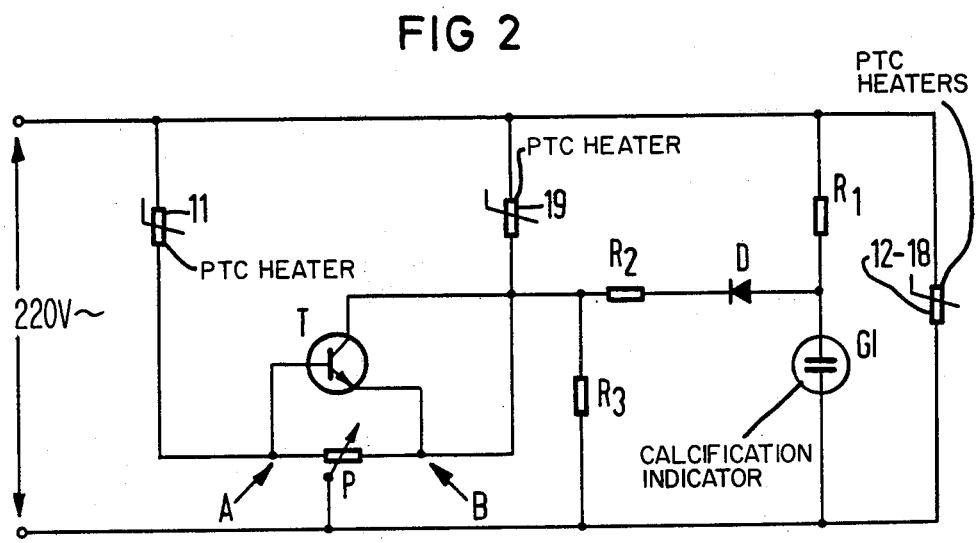
FIG. 2 is a schematic circuit diagram for use in the invention.

FIG. 2 shows a circuit arrangement exploiting the principle of the invention for determining changing, differing current consumption for the electric resistances here referenced K11 and K19, the heating elements 11 and 19 in the area of the water entry or exit, respectively. The resistances of the remaining heating elements 12 through 18 are referenced $K_{12-18}$.

As shown in FIG. 2, a potentiometer referenced P serves for the equalization of initially present potential differences given a condition which is not yet calcified, i.e. for the equalization of the potentials of differing current strengths in the resistances K11 and K19. Such potential differences to be equalized are based, for example, on a spread between units. The potentials of the points A and B, i.e. the fixed connections of the potentiometer P, are compared with one another with the transistor T connected to potentiometer P by its emitter and base. Because of a calcification which becomes stronger and stronger in the area of the water exit, i.e. in the area of the heating element 19 and, thus, for the resistor K19 during the course of a use duration, an increasing potential difference between the points A and B occurs (after the aforementioned original zero adjustment at the potentiometer tap). This potential difference at the base-emitter input of the transistor T leads to a signal voltage at its collector output by which a glow lamp G1 is caused to light up via a resistor network R2, R3 (for adapting the signal voltage to the glow lamp), a diode, and a dropping resistor R1 connected to supply voltage to G1. The supply voltage is indicated at 220 Volts, but can, as required, also be 110 Volts, etc. If necessary, a display device which functions reliably with a corresponding different voltage may be employed in place of a glow lamp G1. Instead of a transistor T (and the diode D), such a circuit can also be equipped with a thyristor.

Figure 3:
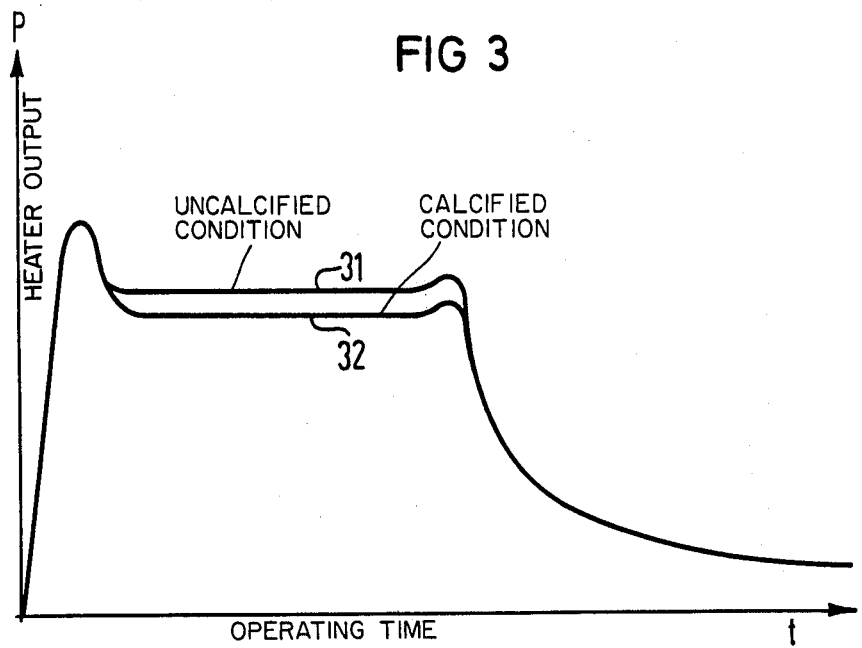
FIG. 3 is a graph for explaining concepts of the invention.

FIG. 3 illustrates a diagram which provides further explanations concerning the principle of the invention. The heat output P is indicated on the ordinate. The operating time t is indicated on the abscissa and the curves referenced 31 and 32 indicate typical curves for the time-dependent emission of heating capacity. Curve 31 corresponds to a coffee-maker which is either not calcified or only insignificantly calcified. The curve 32 corresponds to the heating capacity curve of the same coffee-maker in a calcified condition. The curves illustrate the respective operating conditions. In the invention, the circumstance has been exploited that a curve corresponding to curve 31 is illustrative of the water entry region, i.e. in the region of the heating element 11, since only a minimum calcification occurs there even over lengthy use. On the other hand, a much stronger calcification relative thereto occurs in the water exit region, i.e. in the region of the heating element 19, during use of the device, so that a transition from the condition of curve 31 to the condition of curve 32 occurs there. The current difference arising from the output difference which can be read between the curves 31 and 32 leads to the aforementioned potential difference between the points A and B of FIG. 2 in the course of time.

Although various minor modifications may be suggested by those versed in the art, it should be understood that we wish to embody within the scope of the patent warranted hereon, all such embodiments as reasonably and properly come within the scope of our contribution to the art.

We claim as our invention:

1. An electronic calcification indicator for a flow heater for determining a change of condition which arises in the flow heater because of increasing calcification, comprising: a flow heater heated by separate PTC resistors forming heating elements; one of said PTC resistors being provided at least at a region of water entry and at a region of water exit with each having a separate current supply line; an electrically operated display device operative by a signal; and circuit means connected to the display device for determining when a relative current difference in the current supply lines of the entry and exit region PTC resistors with respect to one another exceeds a predetermined amount so as to create a signal for activating the display device indicative of increased calcification of the exit PTC resistor element relative to the entry element.

2. An electronic calcification indicator according to claim 1 wherein the current supply lines of the entry and exit resistors connect to respective fixed connections of a potentiometer, an adjustable connection of the potentiometer connecting to a power supply and providing a common electric connection for the two current supply lines so that the entry and exit resistors are connected in parallel to said power supply; and a potential difference between the fixed connections of the potentiometer occurring upon increasing calcification forming a signal voltage.

3. An electronic calcification indicator according to claim 1 wherein the signal is amplified via a transistor and supplied to a glow lamp.

4. An electronic calcification indicator for a flow heater for determining increasing calcification of the flow heater, comprising: a flow heater having at least a first PTC resistor as a heating element located at a water entry of the flow heater and a second PTC resistor forming a heating element at a water exit of the heating element; the first and second PTC resistors having separate current supply lines connecting in parallel to a power supply; electronic circuit means for determining a current difference in the separate current supply lines with respect to one another as a result of increasing calcification of the flow heater; and an indicator means connected to the circuit means for indicating a predetermined calcification condition when the circuit means detects a current difference which exceeds a predetermined maximum.

5. The indicator of claim 4 wherein a PTC resistor is provided as a main heating element positioned between the water entry and water exit heating elements.

6. The indicator of claim 5 wherein the separate resistors of the heating elements all connect to a common electrode derived from a common heating element whose resistive layer and top electrode has been subdivided.

* * * * *